US 9,050,556 B1
Jun. 9, 2015

(12) United States Patent
Schieven

(10) Patent No.: US 9,050,556 B1
(45) Date of Patent: Jun. 9, 2015

(54) PLASMA INJECTION AIR FILTRATION SYSTEM

(76) Inventor: Johannes Schieven, Abbotsford (CA)

(*) Notice: Subject to any disclaimer, the term of this patent is extended or adjusted under 35 U.S.C. 154(b) by 204 days.

(21) Appl. No.: 13/565,605

(22) Filed: Aug. 2, 2012

Related U.S. Application Data

(60) Provisional application No. 61/514,588, filed on Aug. 3, 2011.

(51) Int. Cl.
*A61L 9/00* (2006.01)
*C25B 11/00* (2006.01)
*B01D 39/00* (2006.01)
*B03C 3/00* (2006.01)
*B01D 53/34* (2006.01)
*A61L 9/03* (2006.01)

(52) U.S. Cl.
CPC .. *B01D 53/34* (2013.01); *A61L 9/03* (2013.01)

(58) Field of Classification Search
CPC ............ A61L 9/00; A61L 9/03; B01D 53/34; B03C 3/00
USPC ................... 422/22, 186.04, 186.1, 305–306, 422/906–907; 204/164, 176, 280, 288.1; 55/360, DIG. 38; 95/57, 78, 267; 96/15, 96/60
See application file for complete search history.

(56) References Cited

U.S. PATENT DOCUMENTS

| | | |
|---|---|---|
| 2,660,559 A | 8/1949 | Prime |
| 3,696,269 A | 10/1972 | Hochheiser et al. |
| 4,690,803 A | 9/1987 | Hirth |
| 4,954,320 A | 9/1990 | Birmingham et al. |
| 5,552,125 A | 9/1996 | Chamblee et al. |
| 5,630,990 A | 5/1997 | Conrad et al. |
| 6,139,809 A | 10/2000 | Rodden |
| 6,635,153 B1 | 10/2003 | Whitehead |
| 6,723,293 B2 | 4/2004 | Jensen |

(Continued)

FOREIGN PATENT DOCUMENTS

| | | | |
|---|---|---|---|
| CA | WO 2007/089887 A2 * | 8/2007 | ............... B01J 19/08 |
| WO | WO2007089887 | 8/2007 | |
| WO | WO2008055337 | 5/2008 | |

OTHER PUBLICATIONS

Tetsuji Oda, Koichi Ono and R. Ono, Dept.Electr.Eng., The University of Tokyo, Short Gap Non-Thermal Plasma Performance to Decompose Dilute Trichloroethylene, ICESPEX—Australia 2006, Paper 5C1.

(Continued)

*Primary Examiner* — Monzer R Chorbaji
(74) *Attorney, Agent, or Firm* — Dwayne E. Rogge; Schacht Law Office, Inc.

(57) ABSTRACT

Disclosed herein is a plasma filtration insert assembly having in one example an outer casing comprising; an air inlet; an air outlet; an electric power input; and electric power connector; a transformer bracket coupled to the outer casing; at least one step-up transformer attached to the transformer bracket. The insert in electric communication with the electric power connector; a plurality of substantially parallel dielectric tubes in electric communication with the transformer; at least one grounded plate positioned between each dielectric tube with a air gap there between, and; wherein there is no fluid path between the air inlet and the air outlet except by passing between one of the dielectric tubes and one of the grounded plate. In one form, each grounded plate is v-shaped in cross-section.

11 Claims, 22 Drawing Sheets

(56) References Cited

U.S. PATENT DOCUMENTS

| | | |
|---|---|---|
| 7,294,262 B2 | 11/2007 | Tadlock |
| 2006/0204409 A1 | 9/2006 | Son |
| 2006/0251550 A1 | 11/2006 | Keras |

OTHER PUBLICATIONS

Sulfatreat: The Sulfatreat Process, http://www.sulfatreat.com/The%20SULFATREAT%20Process/; Jan. 18, 2011.

* cited by examiner

PLASMA INJECTION AIR FILTRATION SYSTEM

This disclosure claims priority to U.S. Patent Application 61/514,588 filed on Aug. 3, 2011 and incorporated herein by reference.

BACKGROUND OF THE DISCLOSURE

Field of the Disclosure

This application relates to the field of air filters that produce plasma (oxygen radicals, hydroxyl radicals, ions, ozone) which react with the airflow to rapidly oxidize contaminants (odors, bacteria, viruses, etc.) in the airflow prior to atmospheric venting or recirculating.

SUMMARY OF THE DISCLOSURE

Disclosed herein is a plasma filtration insert assembly in one form comprising: an outer casing which in turn comprises; an air inlet; an air outlet; an electric power input; and electric power connector. In one form a transformer bracket is coupled to the outer casing; at least one step-up transformer attached to the transformer bracket and in electric communication with the electric power connector; a plurality of substantially parallel dielectric tubes in electric communication with the transformer; at least one grounded plate positioned between each dielectric tube with a air gap there between, and; wherein there is no fluid path between the air inlet and the air outlet except by passing between one of the dielectric tubes and one of the grounded plate. In one form, the grounded plate is v-shaped in cross-section.

The plasma filtration assembly as described above may be arranged wherein each dielectric tubes in turn comprises: an outer ceramic tube; an inner metal electrode tube; and a central high voltage lead.

The plasma filtration assembly in one form is arranged wherein the outer casing comprises two separable portions comprising: an upper unit housing the transformer bracket and transformers; a lower unit comprising the dielectric tubes and the grounded plates, and; a releasable physical and electrical connection there between.

To ease in installation, repair, and replacement, the plasma filtration assembly may be arranged wherein the outer casing comprises a first half of a bayonet style coupling operatively configured to couple to a second half of the coupling on a cabinet style housing. As such, the assembly may further comprising: a cabinet door, and; an door switch operatively configured to allow electricity to be provided to the electric power inlet of the outer casing only when the cabinet door is closed.

The plasma filtration assembly disclosed herein may be configured wherein each transformer comprises a high frequency, high voltage output to the dielectric tubes.

To aid in retrofit of the plasma filtration assembly to existing structures, the outer casing has a shape and size identical to an existing chemical filter to provide a retrofit thereto when electrically connected to a power source.

To decrease pollutants of a production process, the plasma filtration may be installed wherein the air inlet and outlet of the outer casing is in-line with a vent stack of a production process to filter the air passing there through. In an alternate embodiment, the air inlet and outlet of the outer casing is tangential to a vent stack of a production process to provide plasma into the vent stack which in turn filters the air passing there through.

The term "production process" is used herein to cover airflow from a manufacturing process, HVAC system, food storage location, air supply for hospitals/airports and other locations, residence air supply, and equivalent locations and applications.

The plasma filtration assembly as recited above may be arranged wherein the air outlet of the outer casing in fluid communication with a chemical reaction filter selected from chemical reaction filters which are regenerated by contact with ozone produced by the dielectric tubes.

DESCRIPTION OF THE PREFERRED EMBODIMENTS

Figure 1:
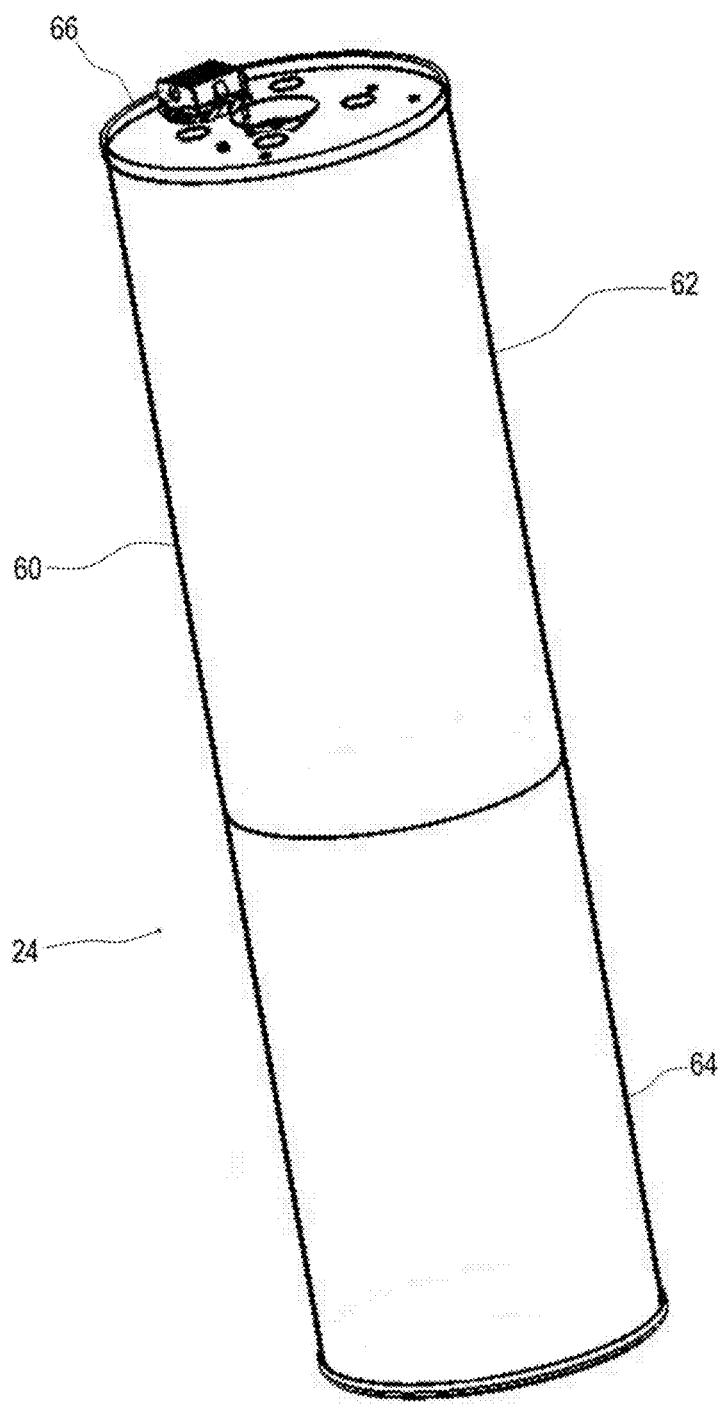
FIG. 1 is an isometric view of one example of a plasma reactor as described herein.

This disclosure relates to the field of controlling odors and/or low concentration (<100 ppm) gasses and/or disinfection by cold plasma injection, or NTP (Non-Thermal Plasma). Since developing the plasma injection technology and treating more than 2,000,000 m3/h (median 17,000 m3/h or 10,000 cfm per system) world wide, this technology has improved to become the most efficient, compact and economical available for many applications.

In one example a small housing of 40×70×75 cm is provided injecting 2,000 m3/h of activated oxygen, converted from clean ambient air with the plasma-injector 22, utilized to inject plasma into a production stack 26 with process airflow 20,000 m3/h and controlling the odor with only 6 kW.

Figure 5:
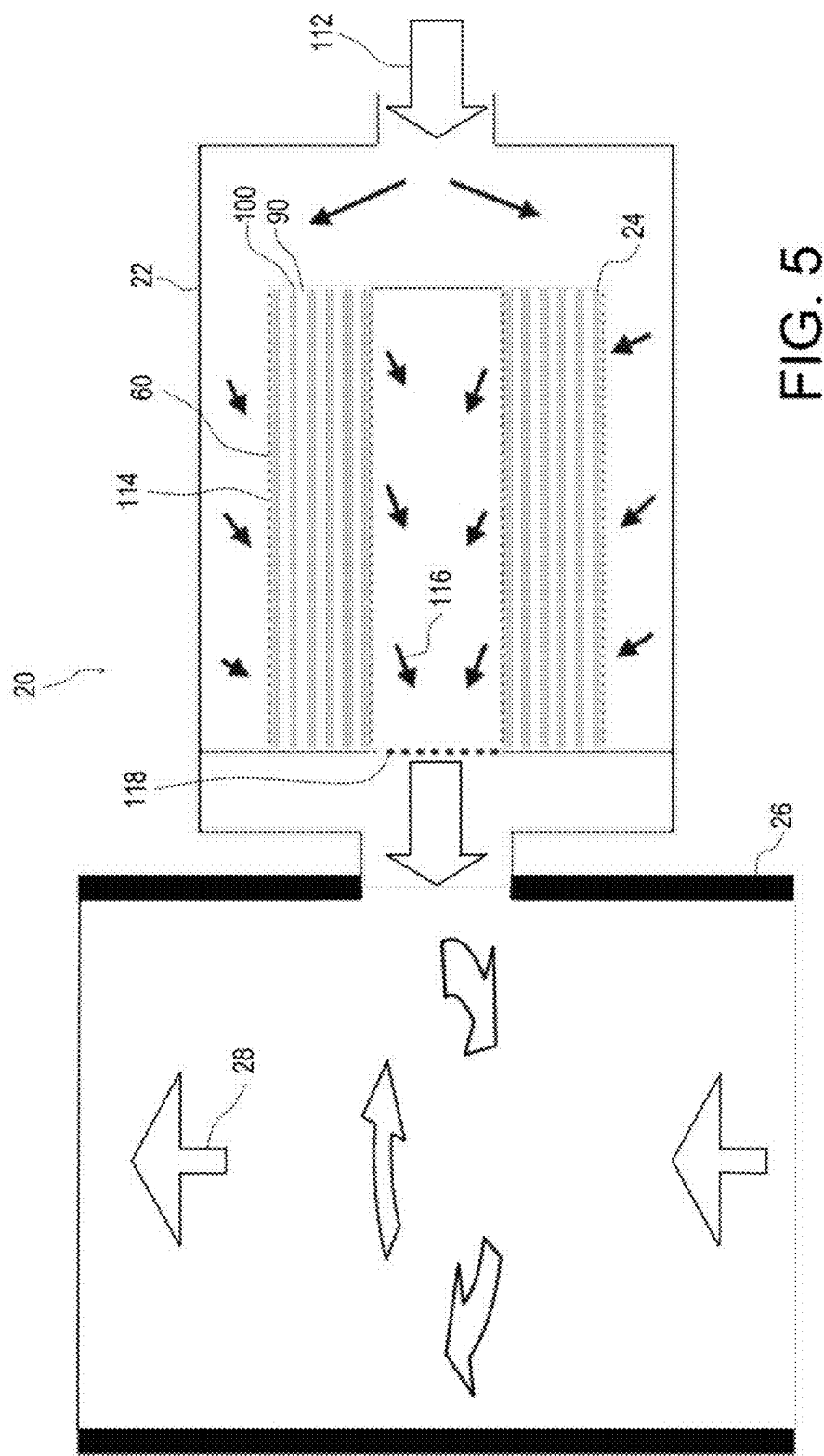
FIG. 5 is a highly schematic view of one mode of use of the disclosure.

In one form, no chemicals, biomaterial, masking agents are required to clean the air and no significant obstructions are present in the process airflow. One example of this is shown in FIG. 5 where the plasma reactor 24 disposes plasma into the stack 26 through an outlet 118. The plasma thus creates a fast oxidation region 142 within the stack 26, reducing the odors components within the airflow 28.

Figure 7:
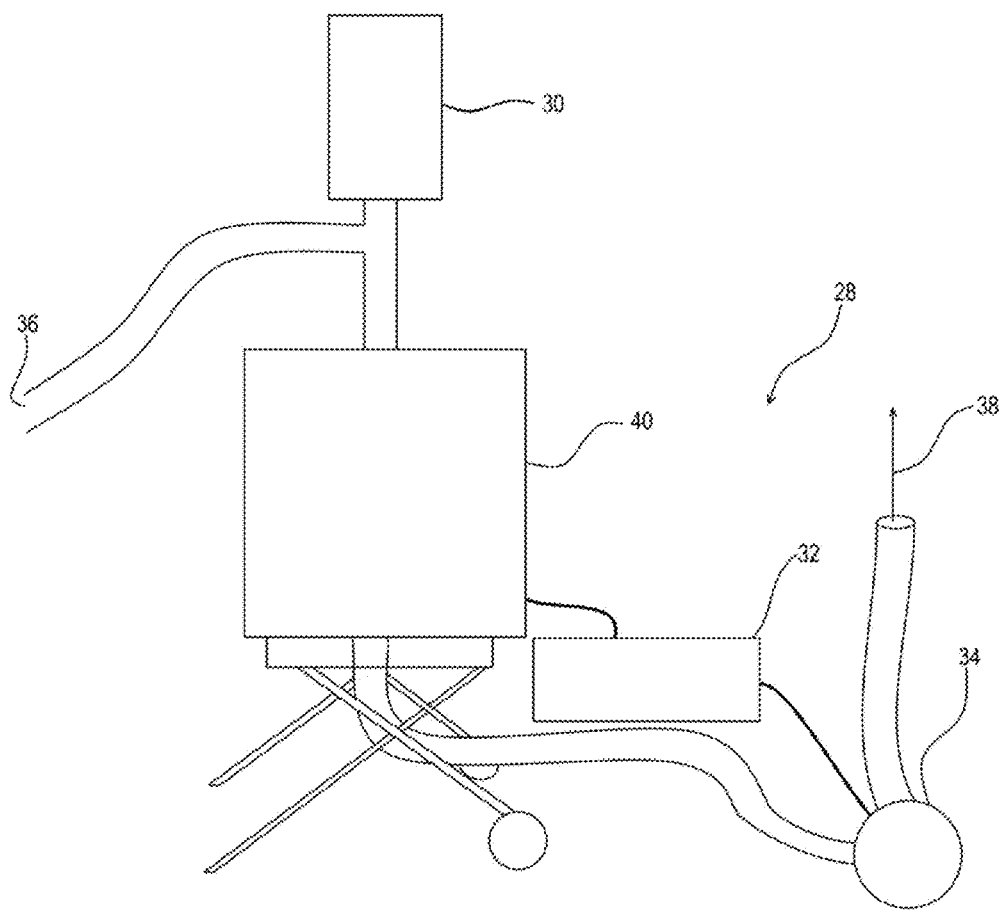
FIG. 7 is a highly schematic view of one operation example of the disclosure.

One disclosed step in the method of using the disclosed odor control method and apparatus may be to evaluate odor reduction requirements with a small pilot demonstration/evaluation unit 28, shown in FIG. 7, at the production site and provide odor dispersion modeling with independent odor labs to demonstrate and provide the required efficiency according to local regulations. The demonstration unit 28 allows for testing and evaluation. A full-scale installation would generally then follow. When fully employed, this full-scale installation often results in no following odor complaints from persons in the surrounding environment.

Figure 4:
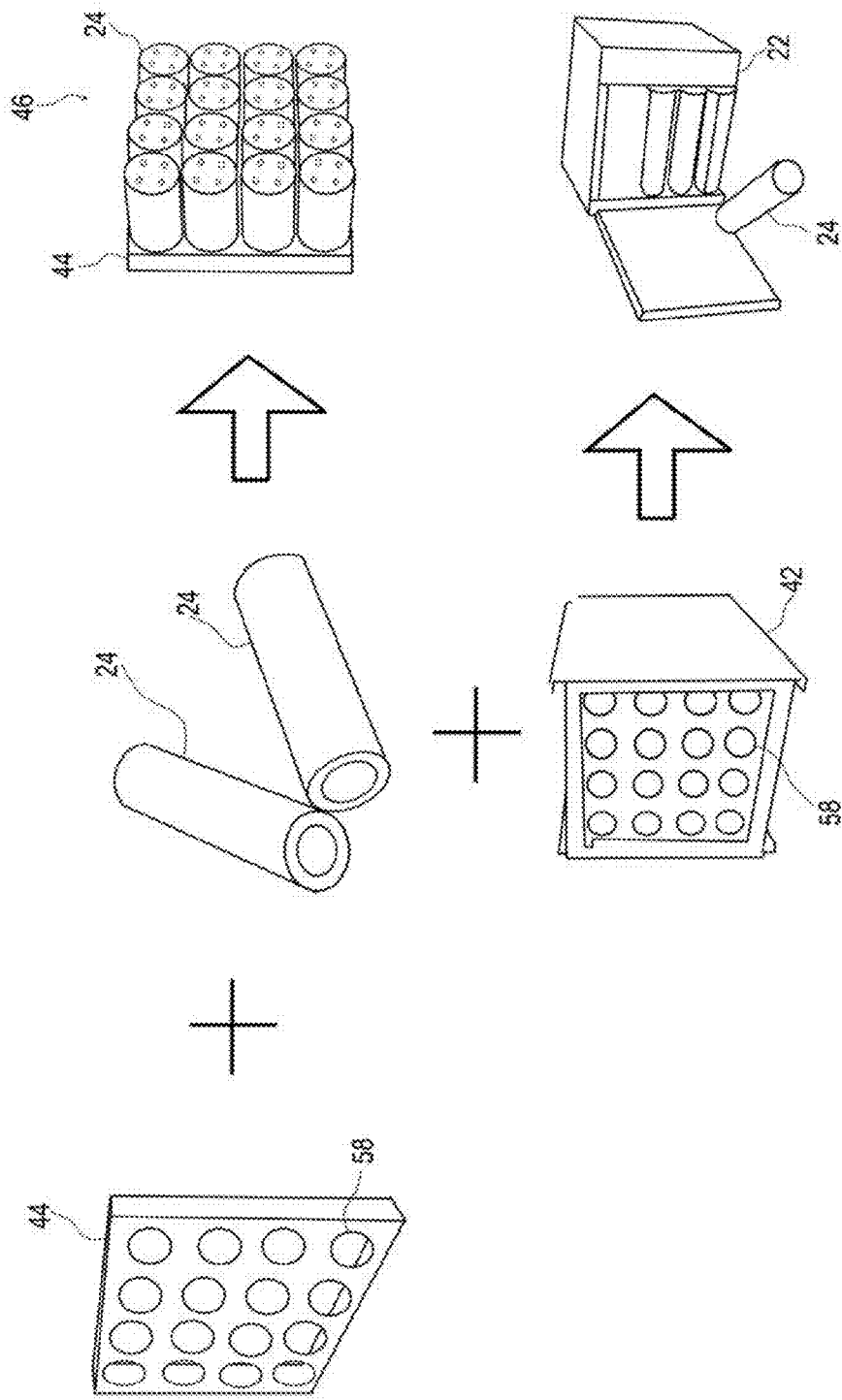
FIG. 4 is a highly schematic view of an installation assembly.

Such a demonstration/evaluation unit 28 may comprise a plasma injector 30 similar to other embodiments described herein. Two examples of such embodiments are shown in FIGS. 1 and 4. A control box 32 may comprise the required circuitry and power supply for the demonstration/evaluation unit 28. A blower 34 may be utilized to provide the desired airflow from the inlet 36 from the stack 26 to an outlet 38. The term stack will be used herein to refer to the ducting used to vent "sour" or contaminated gasses in need of filtering. A cabinet 40 may be provided to supply the needed space for catalytic oxidation between the plasma injector 30, and outlet 38. Catalysts for higher concentrations of gasses, like volatile organic compounds (VOC's) or mercaptans may be included in the cabinet 40 or elsewhere in the system. The demonstration/evaluation unit may be utilized to determine the efficiency and power required to reduce the sour gas to an acceptable limit.

In one form, oxidation of odors occurs naturally without an additional supply of chemicals and waste production. The disclosed plasma reaction system may accelerate this process, to reduce unwanted chemicals beyond the stack 26. Since most odor emissions are a unique cocktail (combination) of odor components, the disclosed plasma-injector can apply a dedicated amount of oxidation power for odor control.

Deodorization by the disclosed plasma-injector, in one form, is facilitated by high-speed oxidation. The oxidized molecules generally cannot be detected organoleptically, hence they do not bother the observer.

One embodiment of a plasma-injector assembly 22, as shown in one form in FIG. 4, consists of a cabinet 42 with plasma reactors 24 provided therein. Ambient air is radiated there through and, as a result, the oxygen and water vapor molecules are dissociated.

Figure 6:
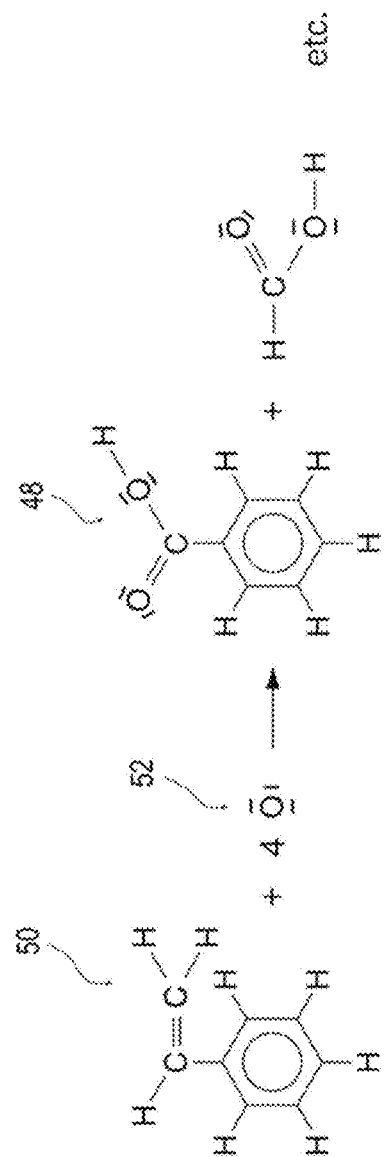
FIG. 6 is a chemical diagram of one use of the disclosed apparatus and system.

This transition (disassociation) may be the first step in a process where an extremely reactive gas is formed, comprising a mixture of instable oxygen and hydroxyl atoms, ions, radicals etc., with elevated electron energy levels. This gas 52, often called 'active oxygen,' has the ability to execute a high-speed oxidation process 48 with the odor components 50 after injection in the polluted air. Such an oxidation process is shown in FIG. 6. While one particular odor molecule (component) 50 is shown for reference, the proposed apparatus and method operates on many odor molecules.

The odor component 50 will lose the faculty of exciting man's sense of smell through the oxidation process, and thus will not be a nuisance to neighbors or others within the locality of the stack 26.

The plasma-injector system 22, as shown in one form in FIG. 4, utilizes a cabinet 42 with Plasma Reactors 24 positioned therein. Ambient air is radiated therethrough and as a result, the odor component molecules are dissociated.

In one form, a plurality of plasma reactors 24 are attached to a mounting flange 44 forming a plasma reactor module 46, which is inserted into the cabinet 42, forming a plasma injector 22.

Benefits of the disclosed method and apparatus in several examples include:
  High odor removal efficiency with variable power supply 0-100%.
  No mechanical wear as there are no moving parts.
  No supply of harmful chemicals, absorbents, biomaterial etc.
  Substantially no waste.
  Relatively low investment and operational costs compared to equivalent processes.
  No impact from process fluctuations like dust, temperature, humidity etc.
  No impact on the production process.
  Does not obstruct process airflow.
  Almost no maintenance required, only 1 repair per 3,000 hours of operation.
  Lower energy consumption than any other odor control system.
  Simple operation (only on/off), no start-up or shut-down procedure.
  Modular design, easy to adapt to any airflow.
  No exposed high voltage wires or connecters (for example >250V) are present outside the plasma reactor. All high voltage wires and connections are contained safely within the grounded plasma reactor casing.
  Very compact, one embodiment of the disclosure has dimensions of W×H×D=0.40×0.70×0.75 m (16×28×30 inch) and operates at 17,000 m3/h (10,000 cfm).

Figure 17:
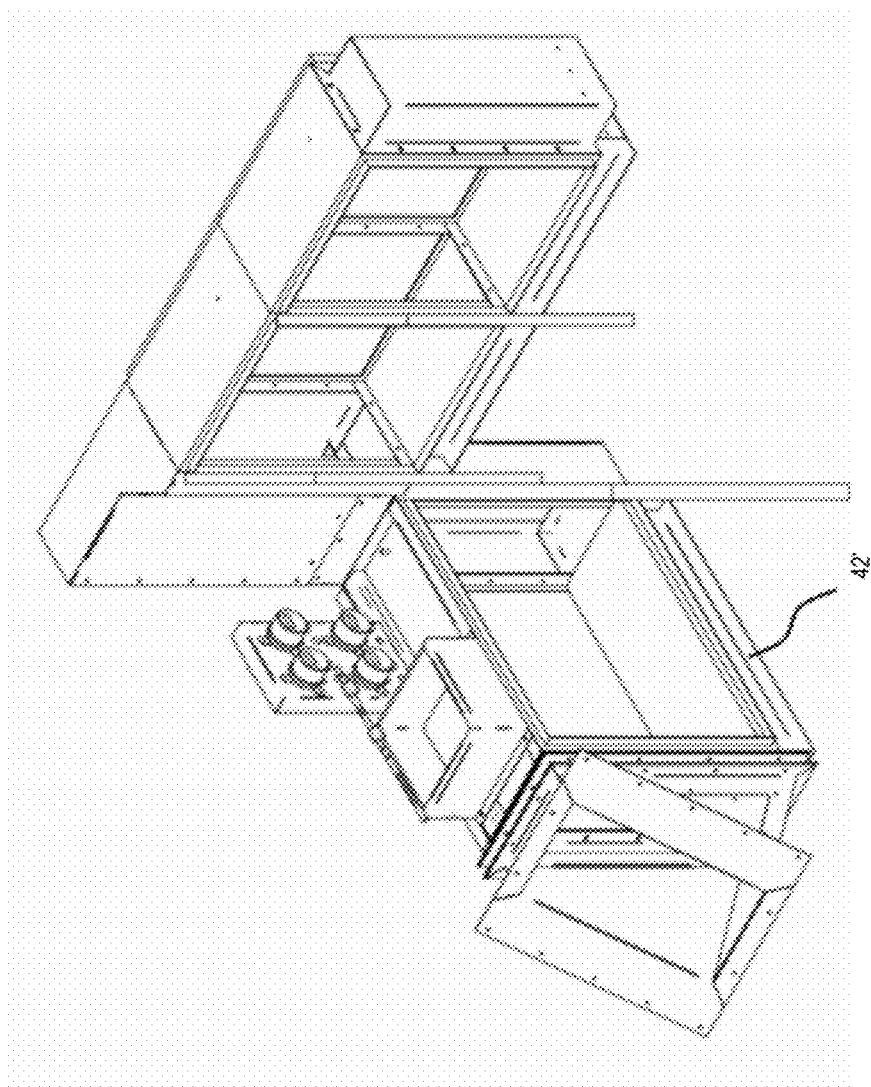
FIG. 17 is a highly schematic view of one mode of use of the disclosure.
Figure 18:
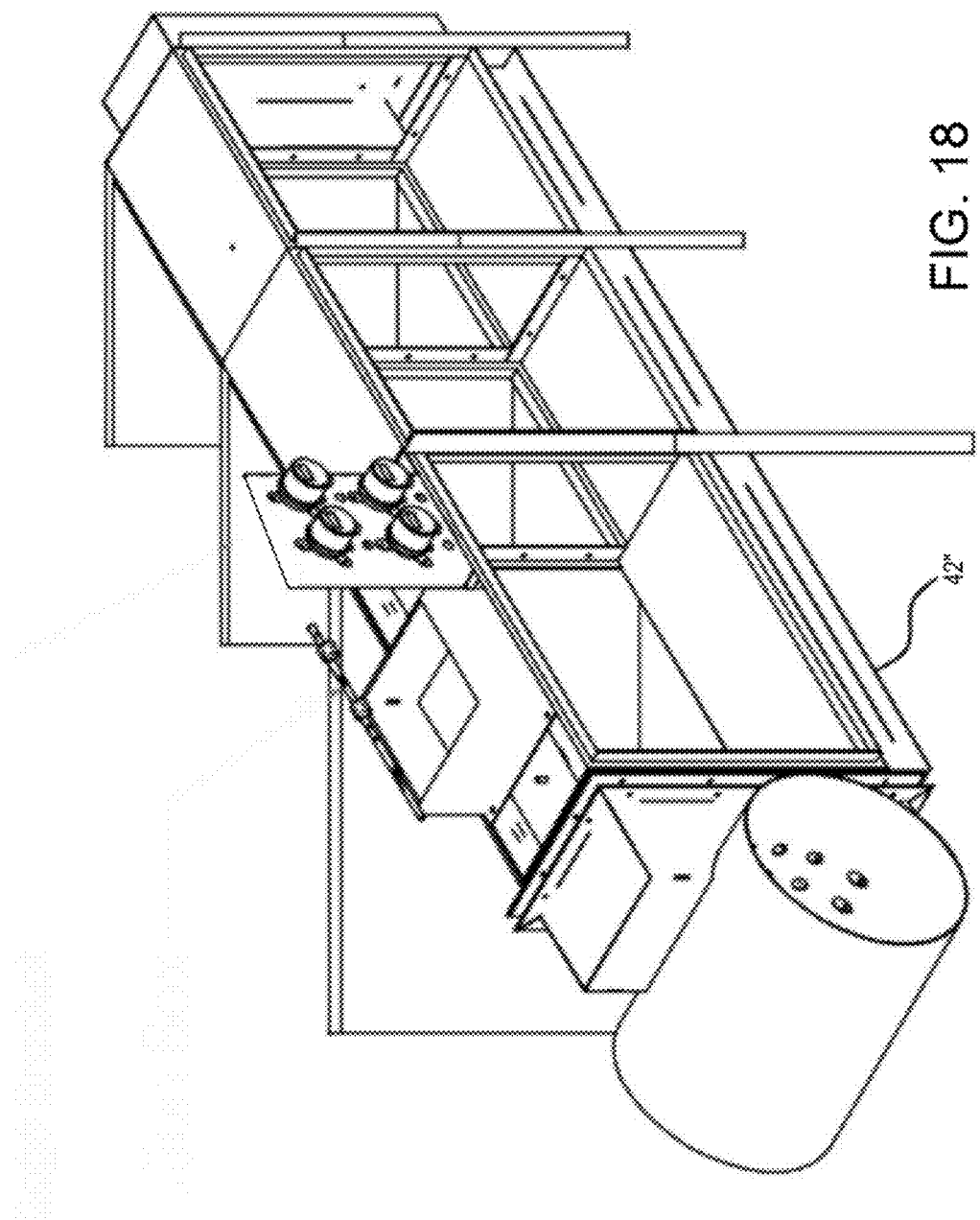
FIG. 18 is a highly schematic view of one mode of use of the disclosure.

Referring again to FIG. 4, filter-holding cabinets 42 are commonly found in the art and field of chemical or obstruction style filters. An implementation utilizing retrofit plasma reactor into an existing cabinet 42 and, in some instances, an existing mounting flange 44 (FIG. 4) results in cost savings, space savings, and other improvements due to the reduced modifications needed to implement the improved design. Looking to FIG. 1, such a retrofit plasma reactor 24 is shown, comprising a bayonet style mounting assembly, so as to be coupled to the mounting flange 44 and substantially aligned with the opening 58 therein. Other mounting structures may also be used, such as threaded or press-fit structures. The mounting flange 44 with the plasma reactors 24 installed therein may then be inserted into the cabinet 42. This results in a cabinet providing in-line plasma filtration, or tangential plasma insertion into the process airflow (stack), as shown in the cabinet embodiments 42' and 42" of FIGS. 17 and 18 respectively.

Figure 2:
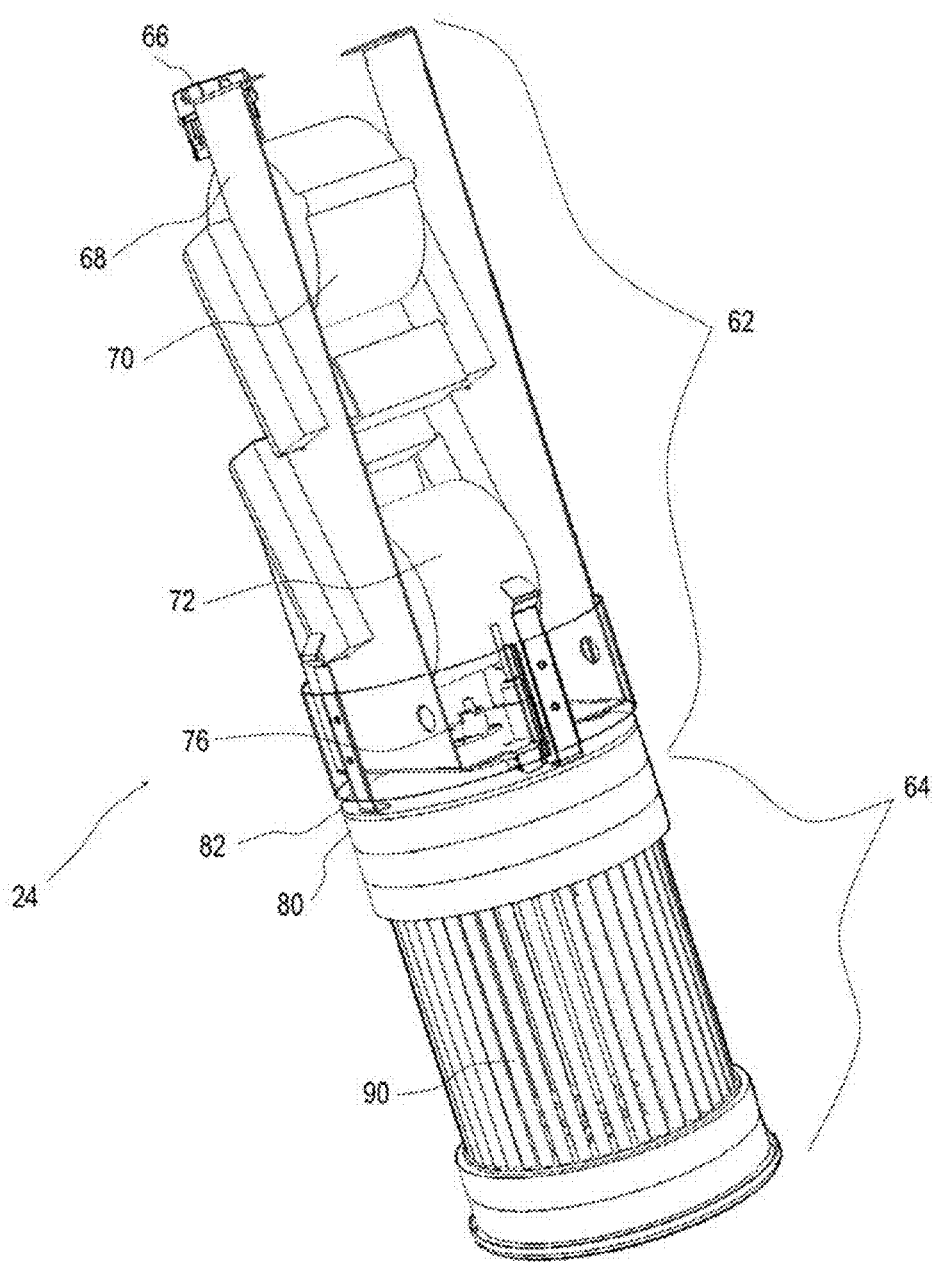
FIG. 2 is an isometric view of the example of FIG. 1 with a portion of the outer casing removed to show the internal components.

Continuing with the description of FIG. 1, the outer casing 60, in one form, includes an upper unit 62 and a lower unit 64, which may have substantially similar outer shapes and diameters. In one form, an electrical, quick disconnect 66 is provided, which can be seen in more detail in FIG. 3. Once the plasma reactor 24 is in place, the quick disconnect 66 allows for simple electrical connection. In one form, the lower unit 64 of the outer casing 60 also provides an air conduit, which will be described in more detail. The air conduit in one example generally includes an inlet in the lower portion between the dielectric tubes and the electrode dividers. The inlet in one example also comprises perforations or a mesh portion of the outer casing 60 surrounding the lower unit 64. In FIG. 2, the plasma reactor 24 is seen with the outer casing 60 removed from that shown in FIG. 1 to more clearly show the internal components. Particularly, the upper unit 62 is shown comprising the electrical quick disconnect 66 previously described, as well as a transformer bracket 68. An upper transformer 70 and lower transformer 72 are shown physically connected to the transformer bracket 68 and electrically coupled to the electrical quick disconnect 66. Of course, while two transformers are shown to provide the desired voltage to the lower unit 64, other arrangements could also be possible. By placing the transformers 70/72 within the apparatus, all voltages outside of the unit can be significantly reduced, increasing the safety parameters of the overall unit. The lower unit 64 is shown connected to the upper unit 62 in a removable manner.

Figure 3:
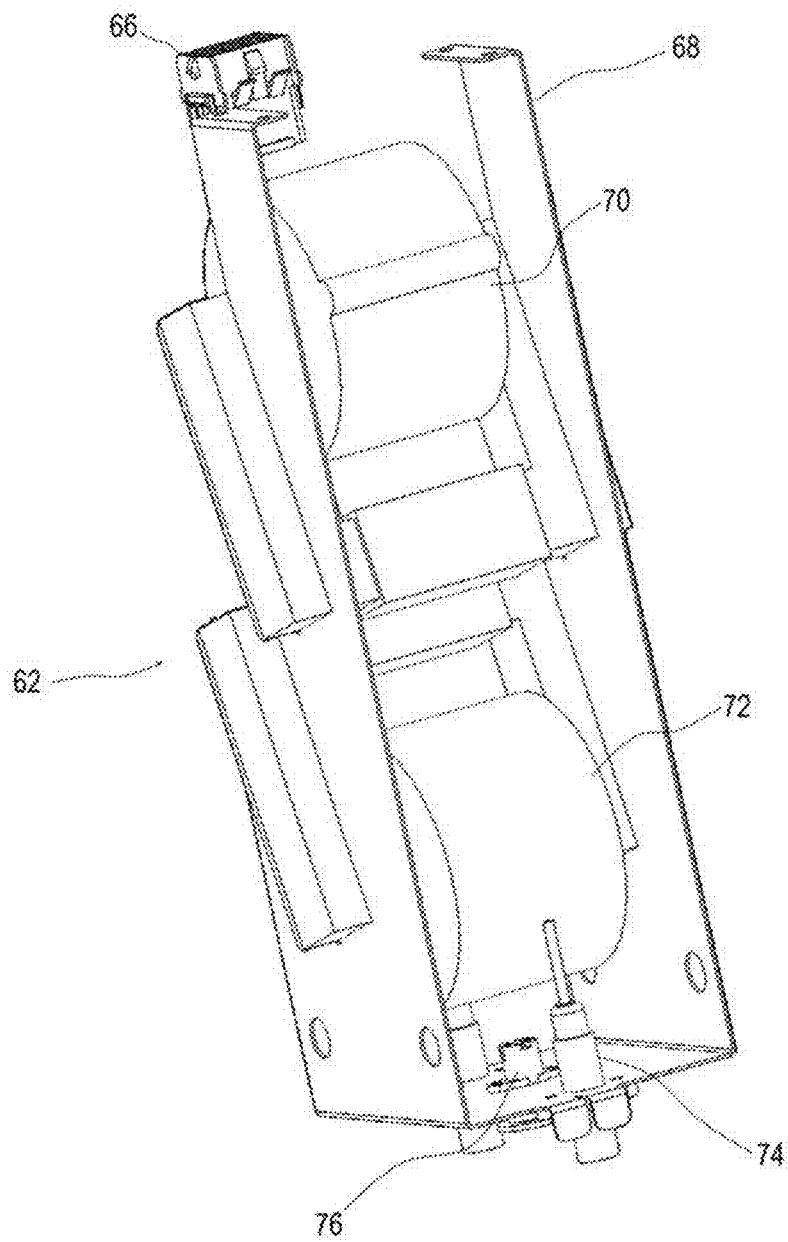
FIG. 3 is an isometric view of an upper unit portion of the example of FIG. 2.

Looking to FIG. 3, the upper unit 62 is shown in more detail, including the components previously described as well as a plurality of female electric couplings 74 and 76, utilized to provide quick electric disconnects between the lower unit 64 and the upper unit 62.

Figure 11:
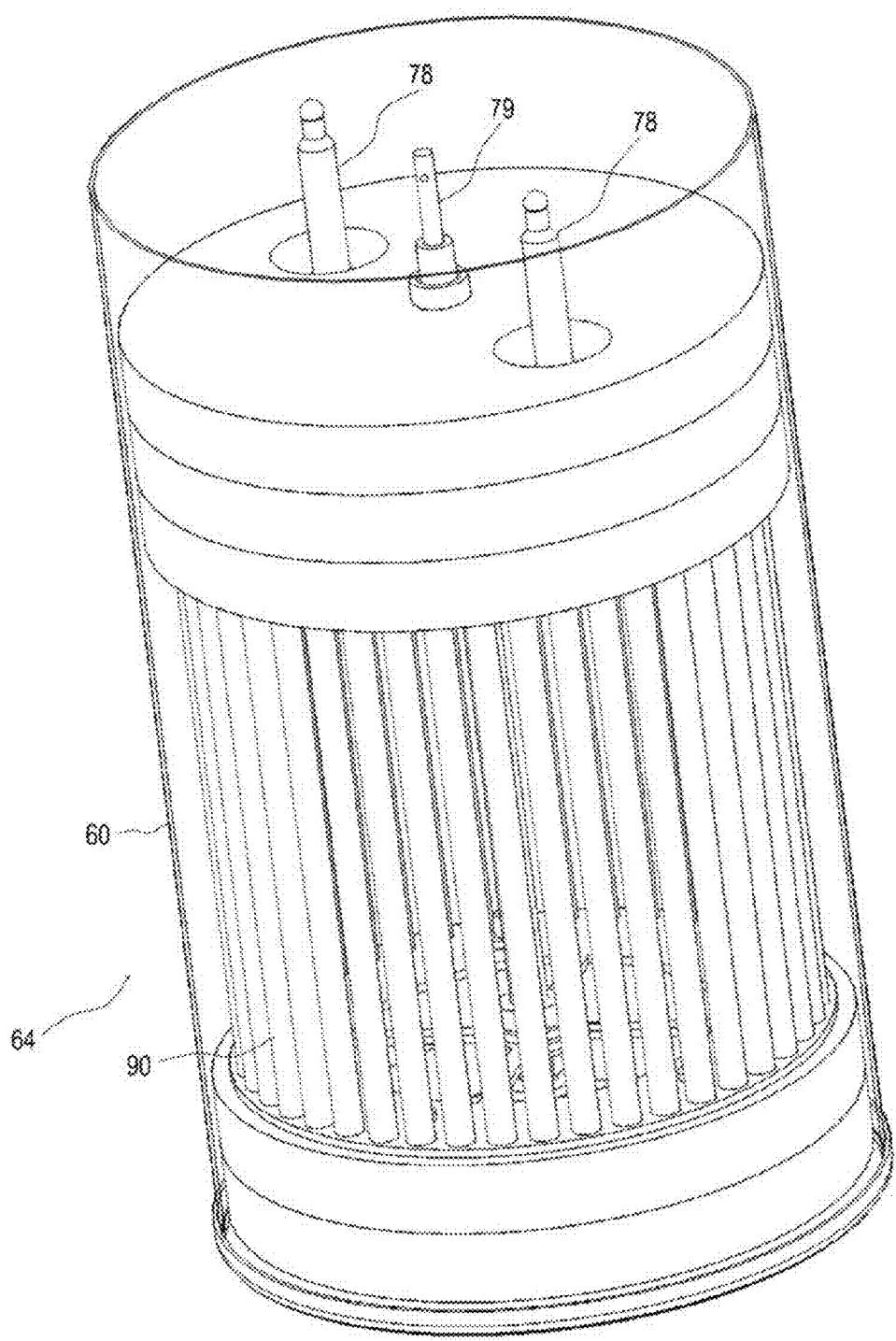
FIG. 11 is an isometric view of a lower unit portion of the example of FIG. 1.
Figure 12:
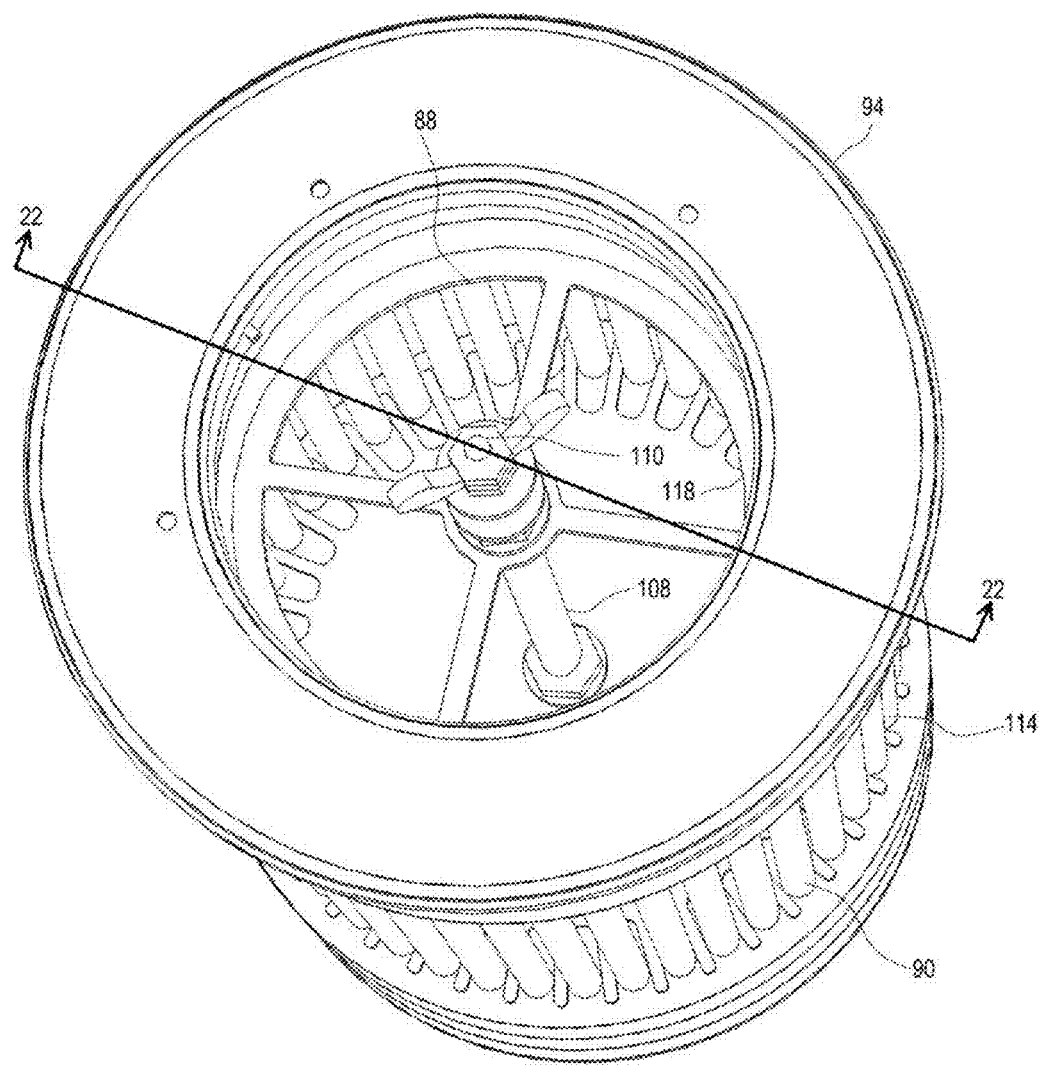
FIG. 12 is another isometric (bottom) view of a lower unit portion of the example of FIG. 1.
Figure 15:
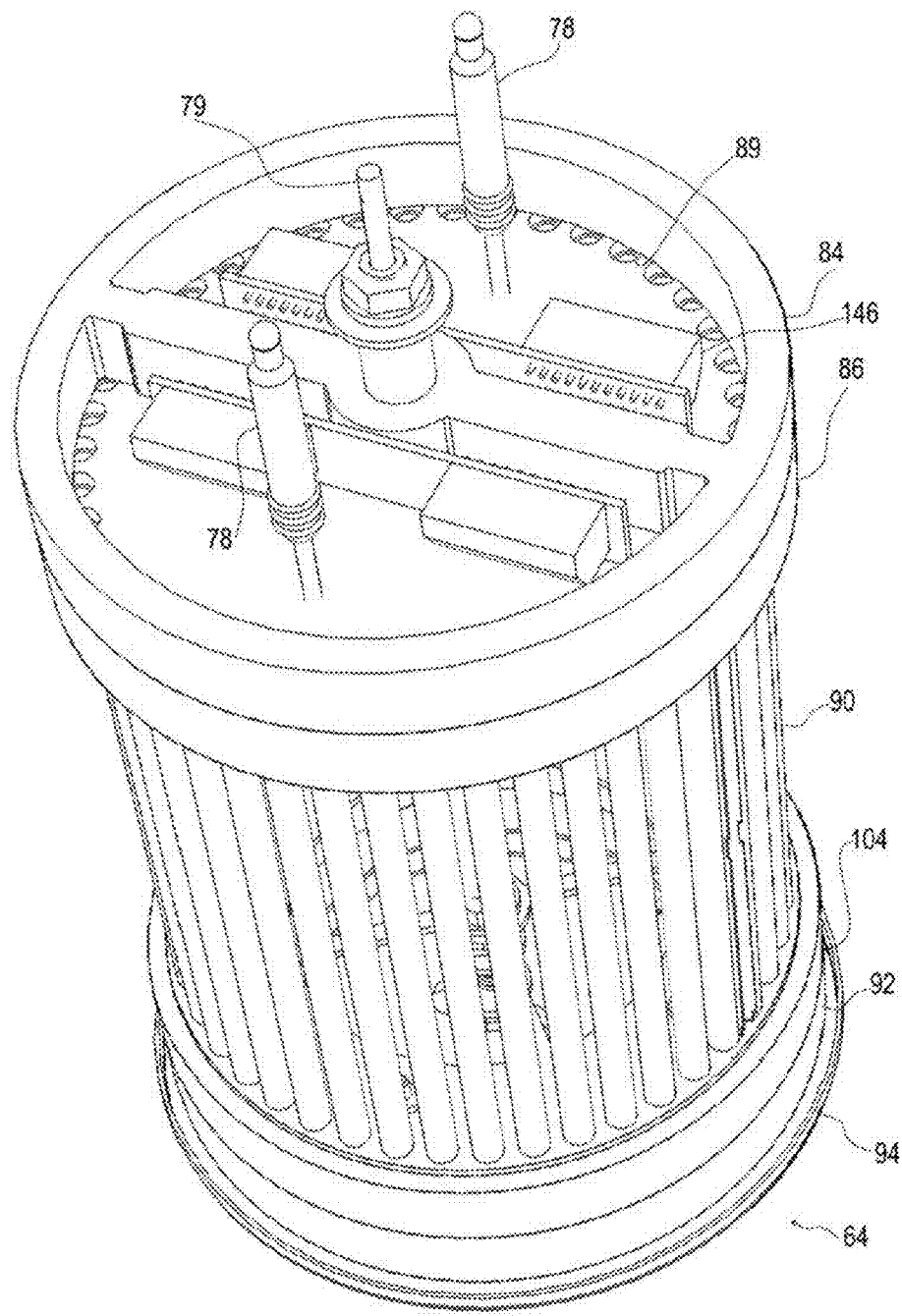
FIG. 15 is an isometric view of a lower unit portion of the example of FIG. 1 with several components removed to show the underlying structure.

Moving on to FIG. 11, there is shown a more detailed view of the lower unit 64 including a plurality of male electric couplings 78 and 79, which can be utilized in conjunction with the female electric couplings 74 and 76 respectively to complete the quick electric disconnect arrangement between the lower unit 64 in the upper unit 62. In addition, the lower section of the outer casing is shown generally transparent so as not to obscure viewing of the internal components. In use, a perforated or mesh material will be used to allow airflow through the lower section of the outer casing. FIG. 15 shows a similar view with the outer casing 60 removed as well as the top cap 80 and connector mounting plate 82, as seen in FIG. 2. This reveals the structure of the top spacer flange 84 and the top tube adapter 86, which comprises a plurality of surfaces defining voids 89. These voids 89 are utilized to align the dielectric tubes 90, which extend from the top spacer flange 84, through the top tube adapter 86, through a bottom tube adapter plate 88, and through a bottom tube adapter 104 to the bottom cap 92. A bottom cylinder flange 94 may also be provided to align the mesh or perforated portion of the outer casing 60 around the lower unit 64. In one embodiment the top cap 80, top spacer flange 84, top tube adapter 86, bottom tube adapter 104, and bottom cap 92 are formed of a nonconductive material such as ceramic or equivalents. FIG. 15 also shows some control circuitry 146 attached to the lower unit 64 within the outer casing.

Figure 19:
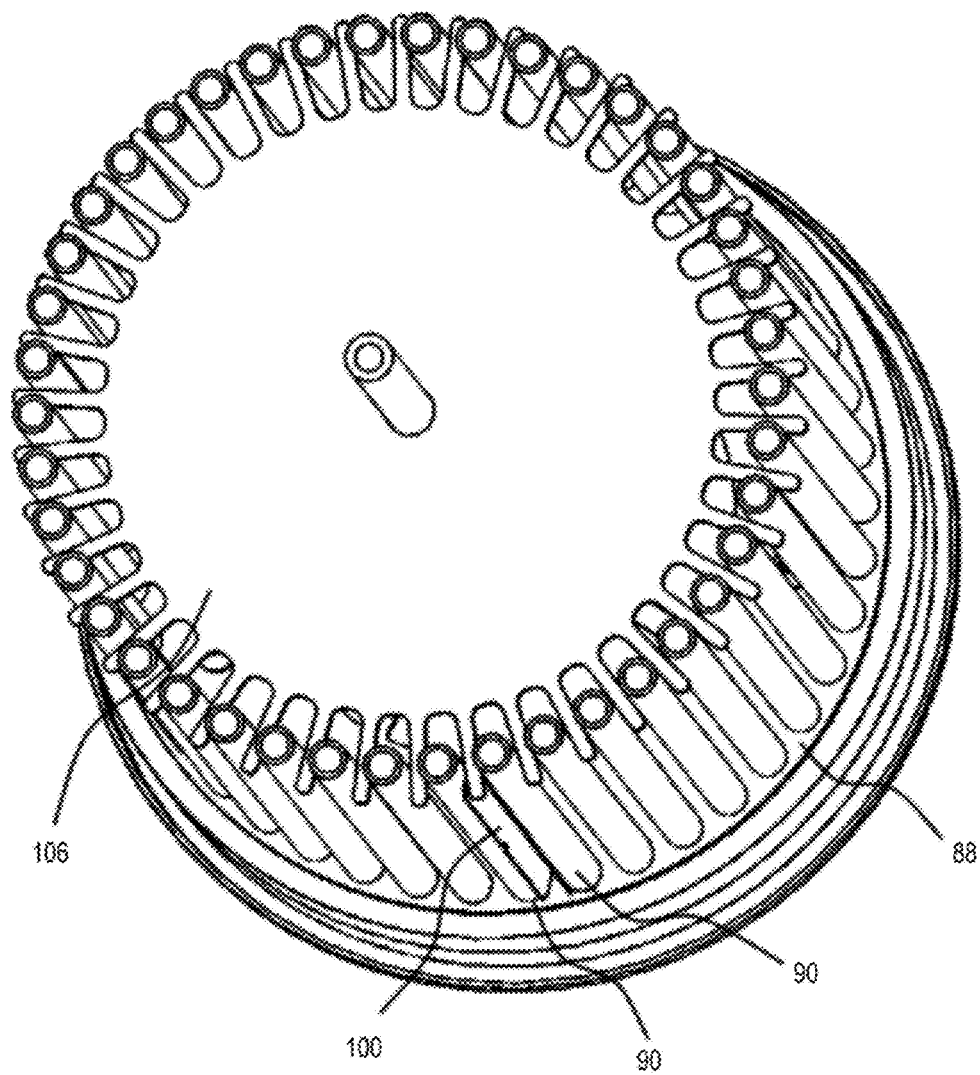
FIG. 19 is an isometric view of a lower unit portion of the example of FIG. 11 with several components removed to show the underlying structure.
Figure 20:
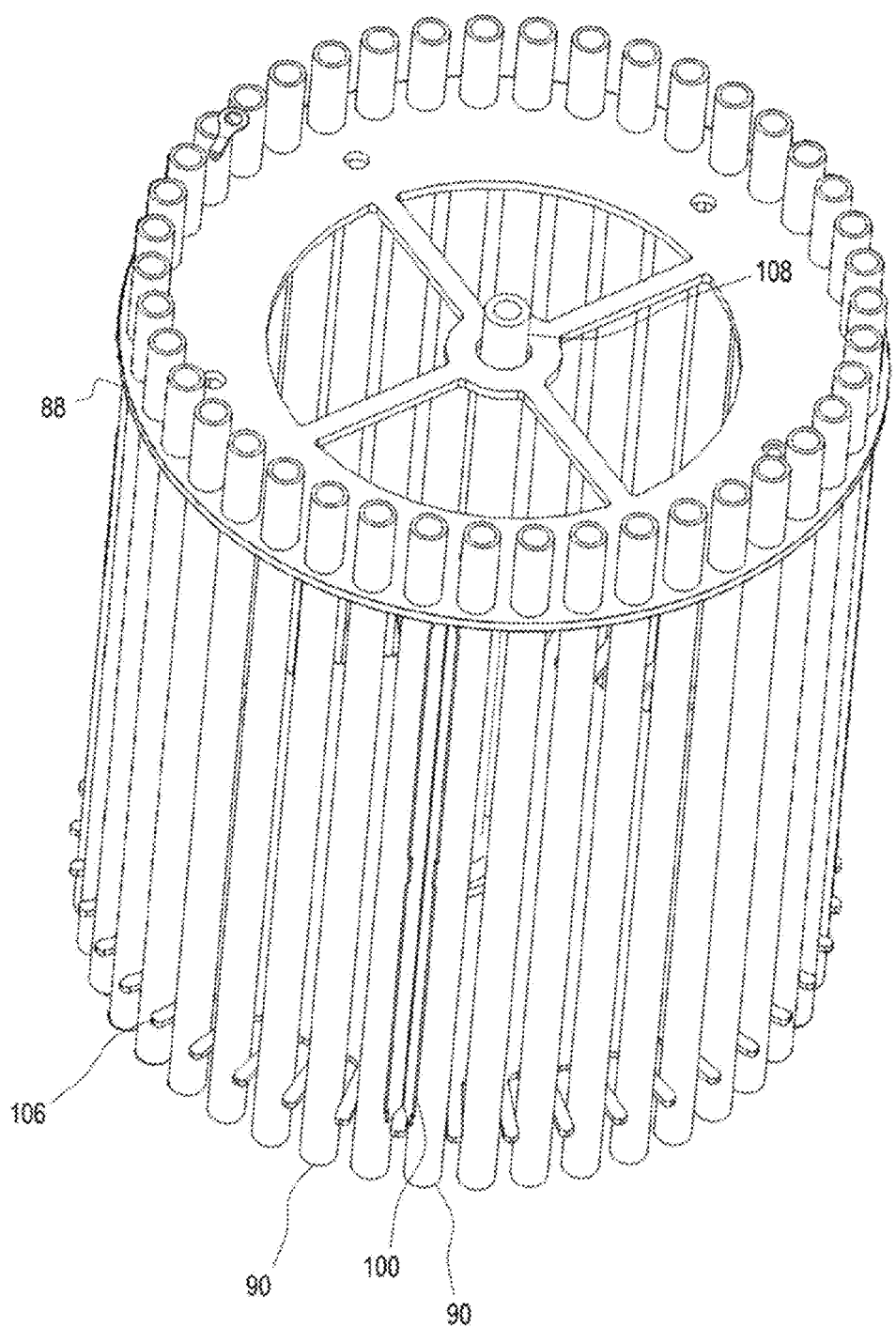
FIG. 20 is an isometric view of a lower unit portion of the example of FIG. 11 with several components removed to show the underlying structure.

FIG. 19 shows several elements removed. A top tube adapter plate 106 is shown, which extends outward to and contacts each of the electrode dividers 100. In this and other Figs., only one electrode is shown, however, it is to be understood that a unique electrode divider 100 would be present between each adjacent dielectric tubes 90. At the other end of the lower section is a bottom tube adapter plate 88, which is shown in more detail in FIG. 20. The top tube adapter plate 106 and bottom tube adapter plate 88 indexes, positions, and electrically couple the electrode dividers 100. In one form, the top tube adapter plate 106 and bottom tube adapter plate 88 are formed of stainless steel to facilitate cleaning, provide a ground for the electrode dividers 100, and reduce oxidation. The central rod 110 may in some applications be coupled to the male coupling 79 previously described. The top tube adapter 106 may be made of spring steel.

Figure 16:
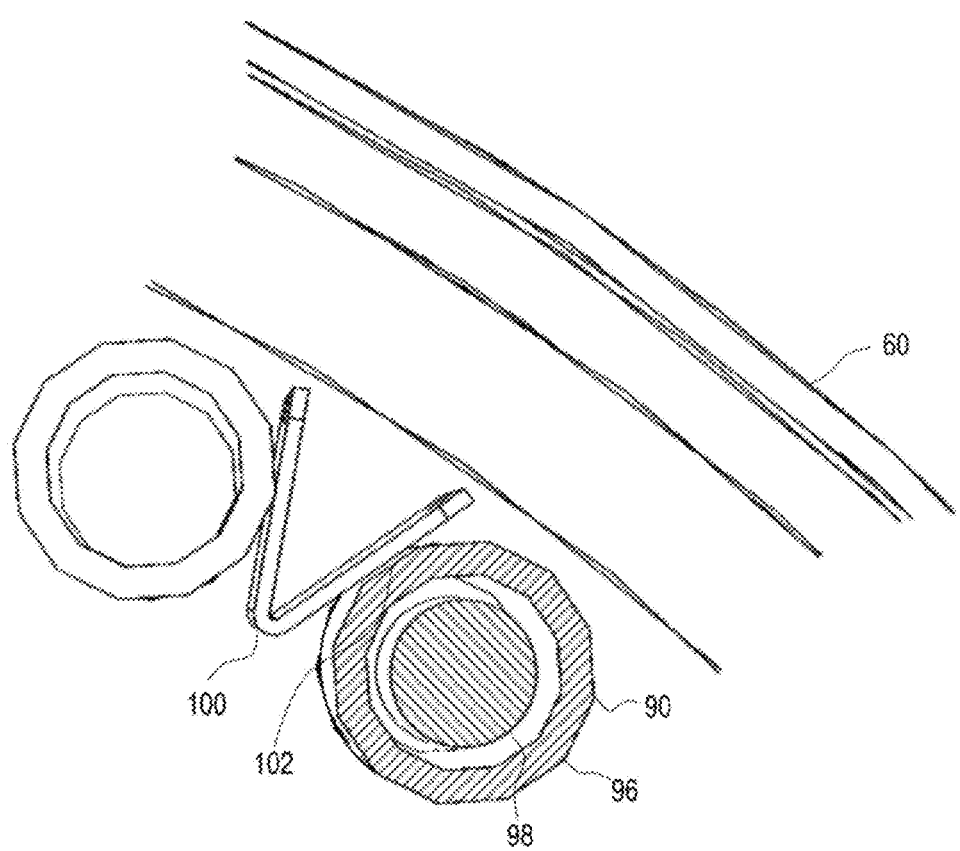
FIG. 16 is a detail view of several internal components of the example of FIG. 1.

Looking to FIG. 16, a detail view of the end portion of two dielectric tubes 90 can be seen along with a portion of the outer casing 60. In one form, the dielectric tube 90 comprises a plurality of concentric elements, including an outer non-conductive cylinder 96 and an inner conductive cylinder or rod 98. This view is highly schematic and does not necessarily show relative diameters of the individual components. In one form, the non-conductive cylinder 96 is comprised of a ceramic material, although other materials could be used. Within the nonconductive cylinder 96 may be provided a conductive rod or cylinder 98, which is electrically coupled to the transformers 70 and/or 72. To function as a plasma (ozone) generator, an electrode divider 100 is provided, which is electrically coupled to ground, thus providing a high voltage e differential between the conductive rod or cylinder 98 and the electrode divider 100. To provide an air passage between the electrode divider 100 and the dielectric tube 90, a gap 102 is provided. In conjunction with the gap 102, the nonconductive cylinder 96 prohibits arcing and physical contact which would result in electrical conductivity between the conductive rod 98 and the electric divider 100, which would be obviously detrimental to operation as a plasma filter. While the gap 102 is difficult to ascertain from this viewing angle, the gap can be understood by one of ordinary skill in the art.

Figure 21:
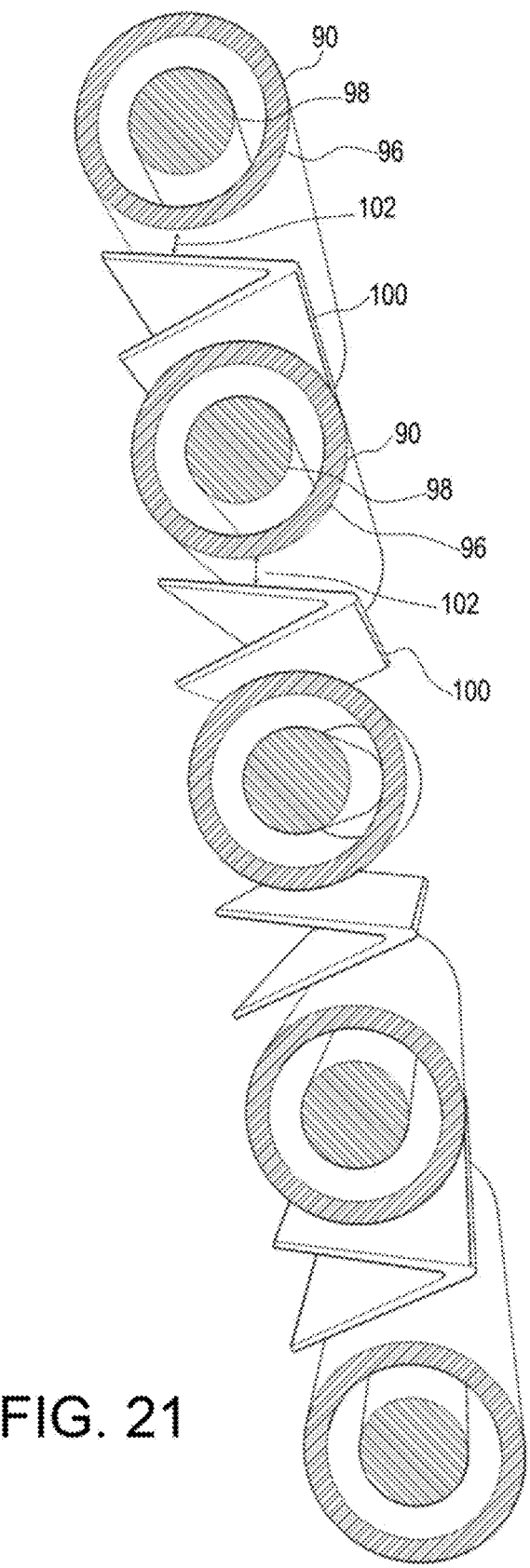
FIG. 21 is an isometric view of a flat (non-cylindrical) example of the disclosure.
Figure 22:
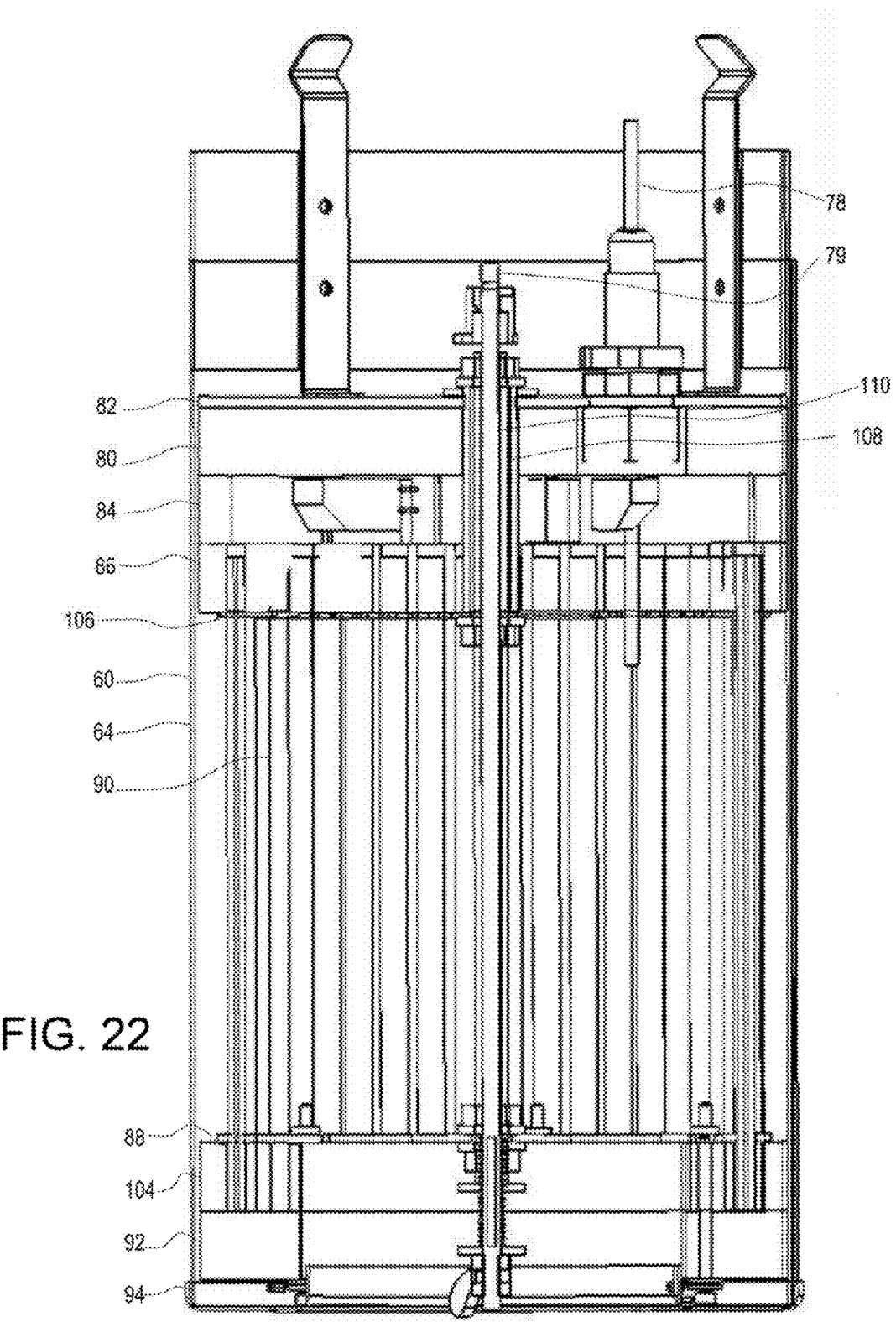
FIG. 22 is a cross sectional view of the lower unit 64 taken along line 22-22 of FIG. 12.

The examples of the electric divider 100, shown in FIGS. 16 and 21, is substantially V-shaped in cross-section. This v-shape allows for a rigid structure with a narrow, substantially linear air gap 102, providing a venturi effect. The V-shape generally provides sufficient rigidity to overcome any bending or twisting effects due to movement, placement, or magnetic/gravitational forces. In addition, testing has shown that as air passes through the gap 102 between the cylindrical outer surface of the nonconductive cylinder 96 and the adjacent surface of the electrode divider 100, a high velocity air region is created within the discharge zone therebetween. Within this high velocity air region, turbulence is generated in the air currents to improve contact between electrons and the air (gas, vapor) and the combination of turbulence and high velocity prevents dirt and pollutants from building up on the surfaces of the dielectric tube 90 and electrode divider 100. The venturi effect increases energy efficiency of the apparatus by reducing the pressure drop over the plasma.

Looking to FIG. 5, it can be seen how ambient air 112 enters the plasma injector 22, and enters the plasma reactor 24 through an inlet 114 which in this embodiment is the mesh/perforated/slotted outer surface of the outer casing 60. The upper unit is not shown in this Fig. The air is activated as it passed between the dielectric tubes 90 and electrode dividers 100 previously described. This activated air 116 then exits the plasma reactor 24 through an outlet 118 wherein it enters the stack 26 resulting in fast oxidation of the reactants (odors) in the region 142 within the airflow 28. This arrangement describes a plasma injector model, which differs from an in-line filtering model in that the process airflow 28 does not pass through the filtering apparatus.

Figure 8:
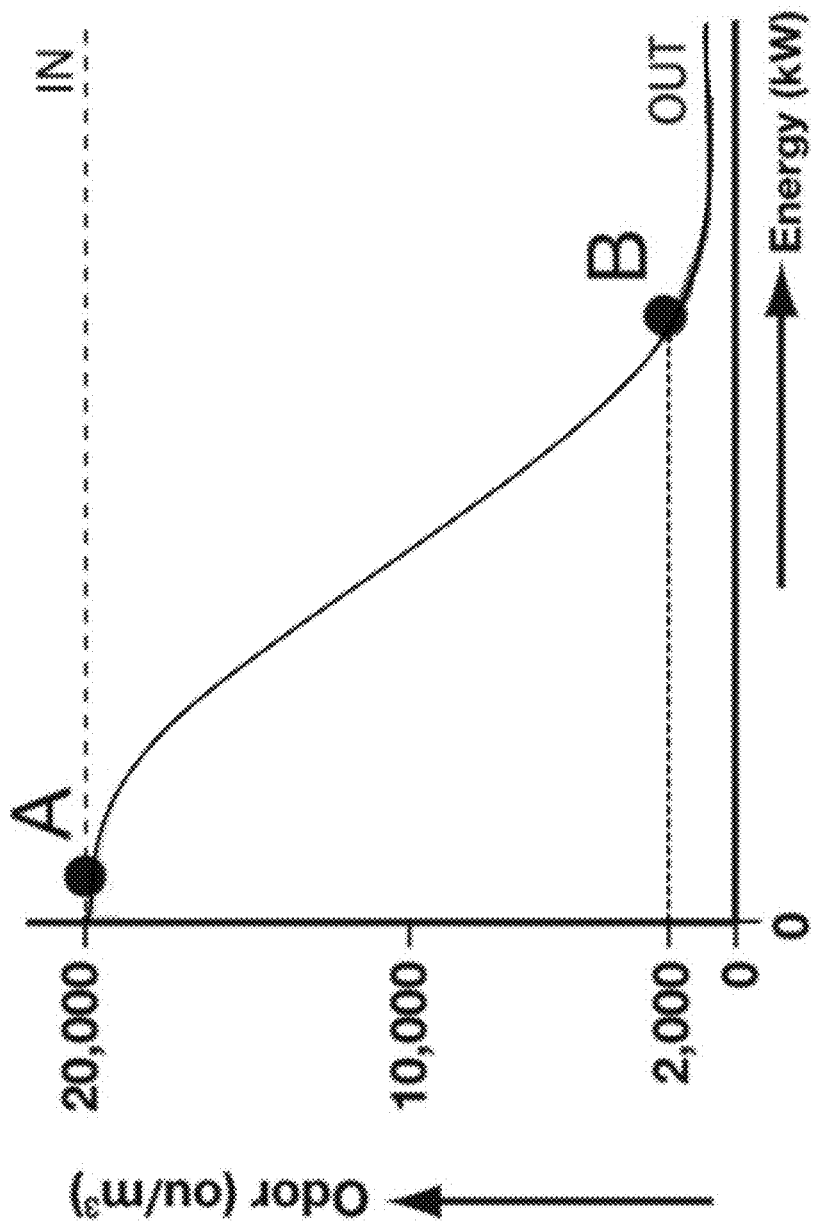
FIG. 8 is a chart which depicts the amount of energy required to decompose odors of differing concentrations.

FIG. 8 shows a graph depicting the amount of energy (plotted on the x-axis) required to filter odor of a particular odor concentration (plotted on the y-axis). Panels of volunteers were used to establish an odor detection threshold.

Figure 9:
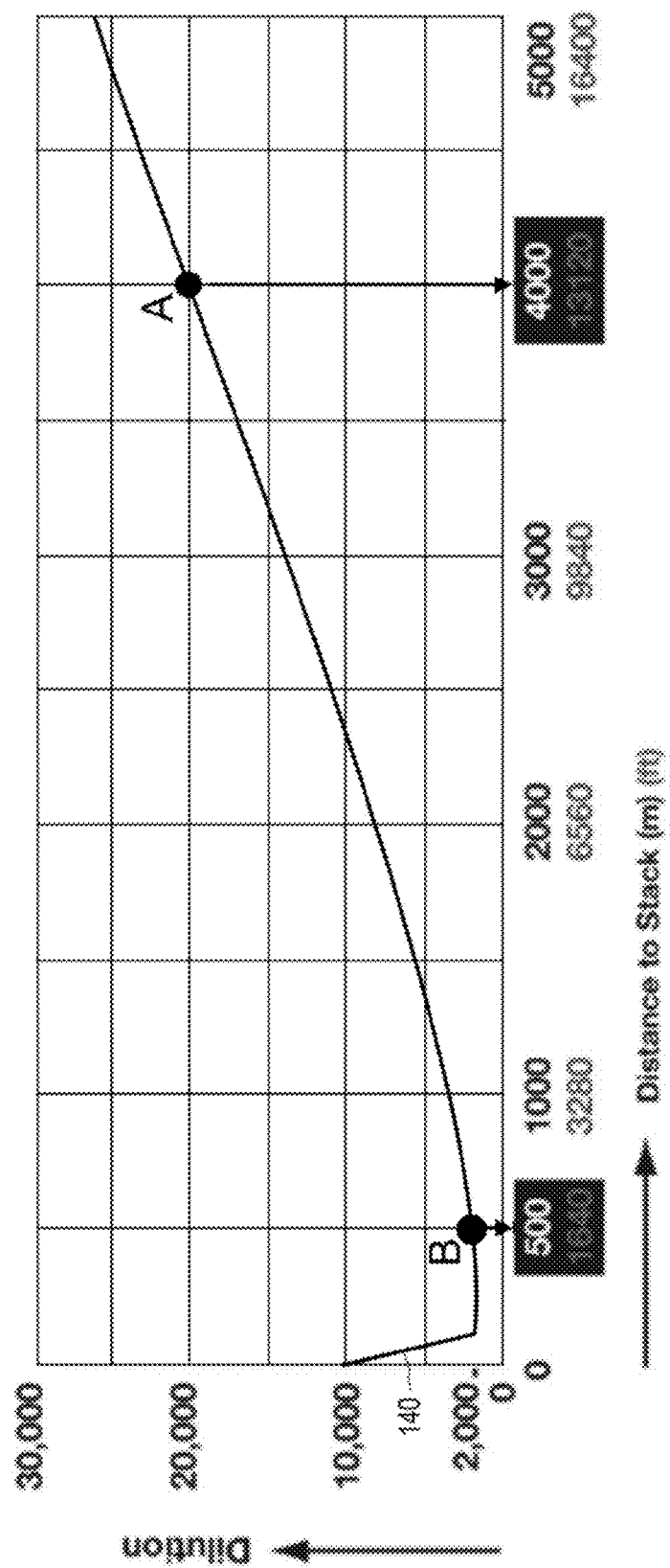
FIG. 9 is a chart which depicts the general relationship between the dilution of an odor as a function of distance to the vent stack.

FIG. 9 shows a graph of a standard dilution versus distance to stack correlation at ground level. The initial slope 140 results from the height of the discharge stack above ground level. The indicator at A shows a detection threshold of an untreated emission at 4,000 meters from the stack. The indicator at B indicates the same odor, wherein the emission is treated, resulting in an odor detection threshold at 500 meters. In simpler terms, the odor of the untreated emission can be detected up to 4,000 meters from the stack, while the treated emission is not organoleptically detectable beyond 500 meters from the stack. This is a result of the decayed odors being much less detectable to a person than the untreated emission. This effect can be very significant where there is a population in the range between 500 meters and 4,000 meters from the stack.

Figure 10:
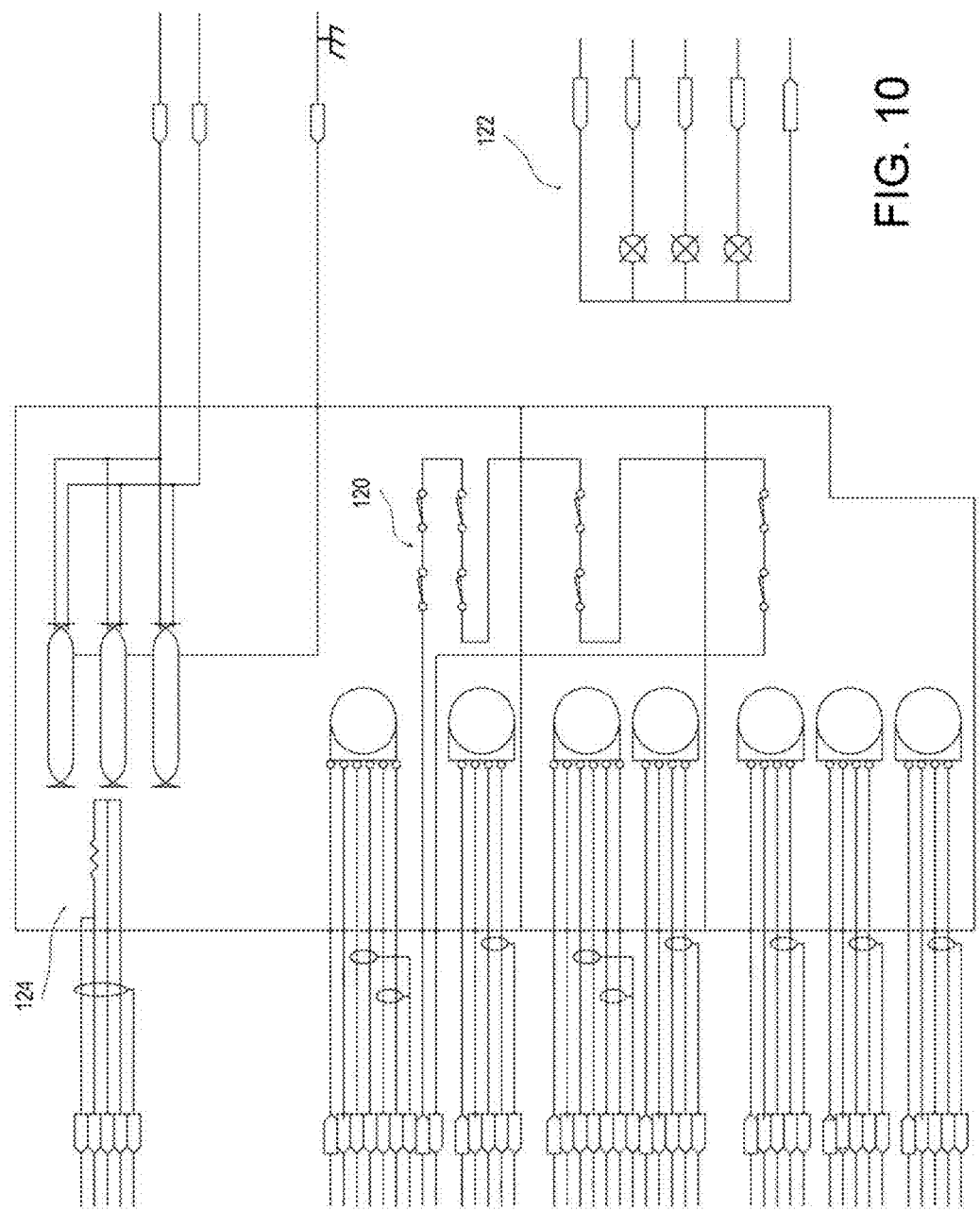
FIG. 10 depicts one example of an electric circuit diagram for a plasma filter cabinet.

FIG. 10 shows the electrical schematic of one embodiment of a cabinet. Of particular interest are the door switches at 120, which electrically disconnect the transformers when the doors are opened. This added safety feature protects users working on or inspecting the plasma reactors. Another safety feature can be accomplished through the example of FIG. 2 in that the high voltage required for plasma generation is present only within the reactor 24. As the transformers themselves are within the reactor, all electric contacts and conductor in the cabinet external to the reactor 24 may be of significantly lower and thus safer voltage. Also shown is an example utilizing indicators (lights) 122, which indicate the status of the apparatus. A temperature sensor 124 may also be utilized to monitor the high voltage transformers. Pressure sensors for (ambient injection) air inlet filter(s) may also be utilized. Temperature and humidity sensors may be added to control a humidifier at air intake, if required, to increase hydroxyl production. Since the high voltage components are insulated, there is no conductive path if condensate/water is present.

Figure 13:
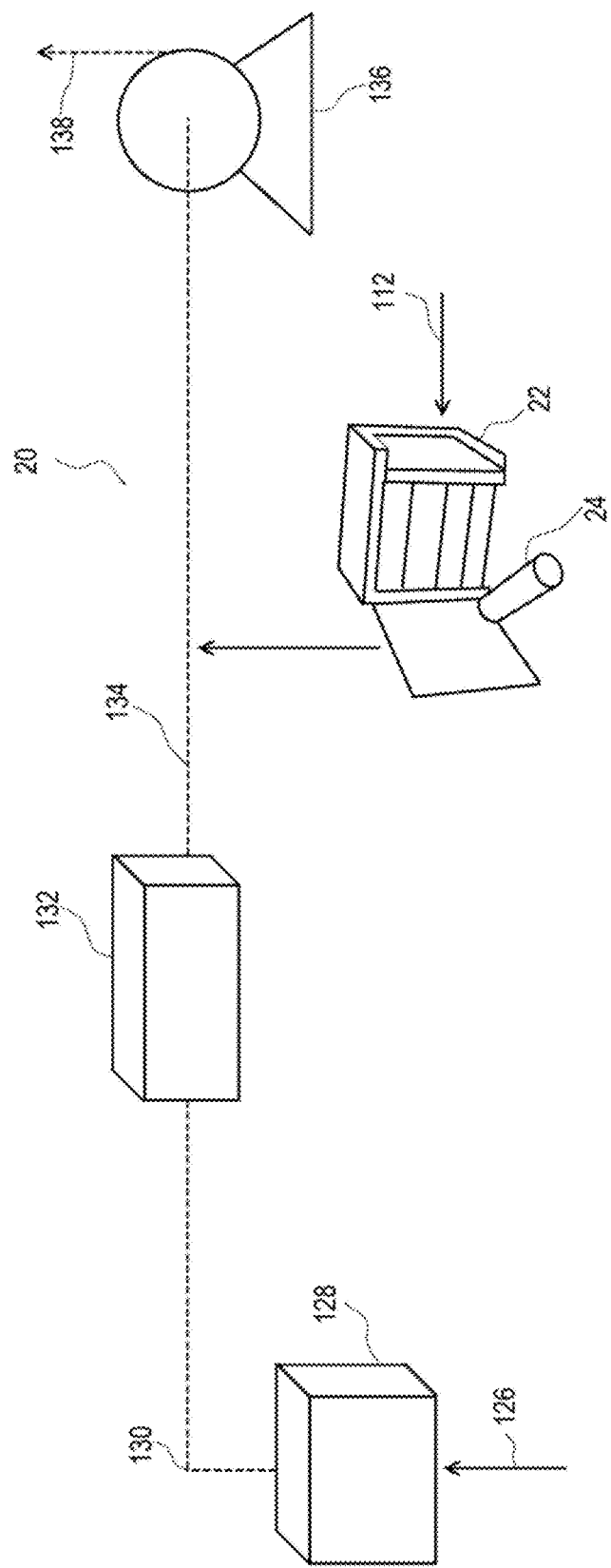
FIG. 13 is a highly schematic flow diagram showing a mode of use of the disclosure.
Figure 14:
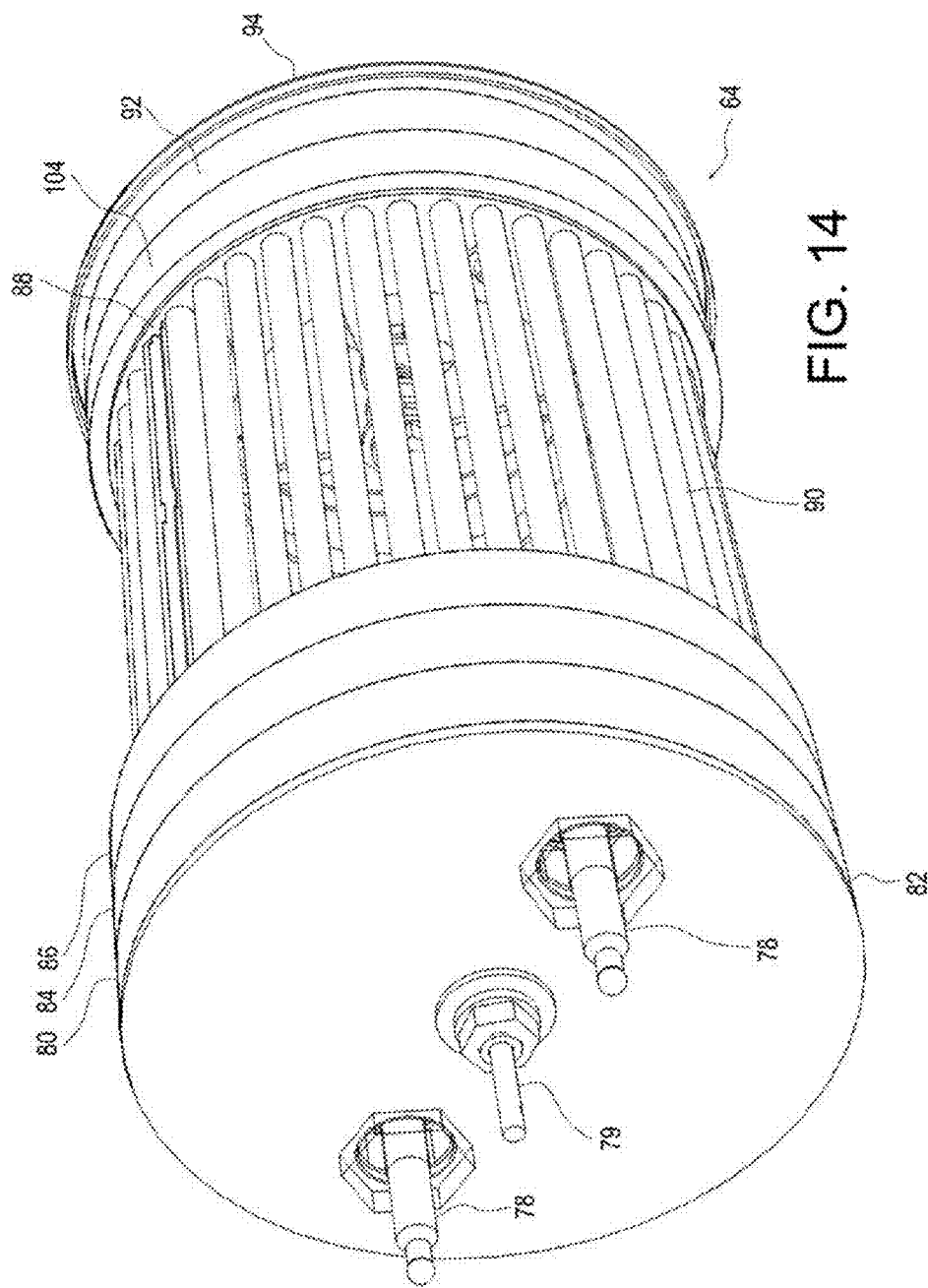
FIG. 14 is an isometric view of a lower unit portion of the example of FIG. 1.

Looking to FIG. 13, a flow diagram of one embodiment of plasma injector system 20 is shown. The first portions of the system include an ambient air inlet 126 providing air to the process 128. The process may be food packing, processing, manufacturing, or other processes that generate undesired odors. The process 128 comprises an outlet 130, which in one form leads to a particle filter 132, such as a cyclone or mesh filter. A plasma injector 22 is shown injecting plasma into the filter outlet 134 where the plasma reacts with the odors therein, which may be vented via an optional catalyst through a blower 136 to atmosphere 138. In a similar example, the plasma injector 22 is provided downstream from the particle filter 132. As mentioned, in some applications the particle filter 132 and/or blower 136 may not be utilized.

FIG. 21 shows an example of another relative positioning of the dielectric tubes 90 and electrode dividers 100 in a planar arrangement rather than the cylindrical arrangement shown in several other examples. As the other components are functionally equivalent, they are not shown in this Fig. This example allows the plasma injector 144 to replace planar obstruction filters commonly found in the art.

While the present invention is illustrated by description of several embodiments and while the illustrative embodiments are described in detail, it is not the intention of the applicants to restrict or in any way limit the scope of the appended claims to such detail. For example, the terms upper and lower transformer are used to distinguish the separate transformers but the terms are not to be interpreted as relative to gravity or any external reference. Additional advantages and modifications within the scope of the appended claims will readily appear to those sufficed in the art. The invention in its broader aspects is therefore not limited to the specific details, representative apparatus and methods, and illustrative examples shown and described. Accordingly, departures may be made from such details without departing from the spirit or scope of applicants' general concept. For example, the sections (units) 62 and 64 may be attached without a quick disconnect, or the section 62 may be installed in a separate control box. Or a (granular or honeycomb) catalytic converter (catalyst) may be placed between cap 92 and flange 94 to oxidize residual (partially oxidized) gas-contaminates and ozone when the plasma system works in-line. When the ozone is decomposed in this process oxygen radicals are generated that will further oxidize the residual gas contaminates.

Instead of the v-shaped ground electrodes, the tubes may be alternating high-voltage and grounded electrodes, eliminating the need for the v-shaped ground electrodes.

Therefore I claim:

1. A plasma filtration reactor assembly comprising:
   A cylindrical filter casing comprising;
      an air inlet;
      an air outlet;
      an electric power input;
      an electric power connector;
      a central axis;
      a transformer bracket coupled to and contained within the filter casing;
      at least one step-up transformer contained within the filter casing, the transformer attached to the transformer bracket in electric communication with the electric power connector;
      a plurality of substantially parallel non-conductive dielectric tubes each substantially equidistant from and parallel to the central axis of the filter casing;
      a conductive dielectric positioned within each dielectric tube in electric communication with the transformer;
      at least one electrode divider positioned between each dielectric tube with a air gap there between, tubes each substantially equidistant from and parallel to the central axis of the filter casing and;
      wherein there is no fluid path between the air inlet and the air outlet except between the dielectric tubes and the electrode dividers.

2. A plasma filtration assembly comprising:
   a filter casing comprising;
      an air inlet;
      an air outlet;
      an electric power input;
      an electric power connector;
      a transformer bracket coupled to and contained within the filter casing;
      at least one step-up transformer contained within the filter casing, the transformer attached to the transformer bracket in electric communication with the electric power connector;
      a plurality of substantially parallel dielectric tubes in electric communication with the transformer;
      at least one electrode divider positioned between each dielectric tube with a air gap there between;
      wherein there is no fluid path between the air inlet and the air outlet except between the dielectric tubes and the electrode dividers; and
      wherein each electrode divider is v-shaped in cross-section.

3. The plasma filtration assembly as recited in claim 2 wherein each dielectric tube in turn comprises:
   an outer ceramic tube;
   an inner metal electrode tube; and
   a central high voltage lead.

4. The plasma filtration assembly as recited in claim 2 wherein the filter casing comprises:
   an upper unit containing the transformer bracket and transformers therein;
   a lower unit comprising the dielectric tubes and the electrode dividers therewithin, and;

a releasable physical connection and a releasable electrical connection there between the upper unit and the lower unit.

5. The plasma filtration assembly as recited in claim 2 wherein each transformer comprises a high frequency, high voltage output to the dielectric tubes.

6. The plasma filtration assembly as recited in claim 2 wherein the filter casing has a shape and size identical to the housing of an existing chemical or barrier filter to provide a retrofit thereto when electrically connected to a power source.

7. The plasma filtration assembly as recited in claim 2 wherein the air outlet of the filter casing is tangential to a vent stack of a production process to provide plasma into the vent stack which in turn filters the air passing there through by way of rapid oxidation.

8. The plasma filtration assembly as recited in claim 2 wherein the air outlet of the outer casing in fluid communication with a chemical reaction filter selected from chemical reaction filters which are regenerated by contact with ozone produced by the dielectric tubes.

9. The plasma filtration assembly as recited in claim 2 wherein the outer casing is substantially cylindrical.

10. A plasma filtration assembly comprising:
   a filter casing comprising;
      an air inlet;
      an air outlet;
      an electric power input;
      an electric power connector;
   a transformer bracket coupled to and contained within the filter casing;
   at least one step-up transformer contained within the filter casing, the transformer attached to the transformer bracket in electric communication with the electric power connector;
   a plurality of substantially parallel dielectric tubes in electric communication with the transformer;
   at least one electrode divider positioned between each dielectric tube with a air gap there between;
   wherein there is no fluid path between the air inlet and the air outlet except between the dielectric tubes and the electrode dividers; and
   wherein the filter casing comprises a first half of a bayonet style coupling operatively configured to couple to a second half of the bayonet style coupling which is provided on a cabinet housing.

11. The plasma filtration assembly as recited in claim 10 further comprising:
   a cabinet door, and;
   an door switch operatively configured to allow electricity to be provided to the electric power inlet of the outer casing only when the cabinet door is closed.

* * * * *